(12) United States Patent
Achenbach et al.

(10) Patent No.: US 6,344,533 B1
(45) Date of Patent: Feb. 5, 2002

(54) SILICONIMIDES CONTAINING SI-H GROUPS

(75) Inventors: Frank Achenbach, Simbach/Inn; Armin Fehn, Emmerting, both of (DE); Pius Tosch, Neukirchen/E (AT)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/463,118

(22) PCT Filed: Jul. 2, 1998

(86) PCT No.: PCT/EP98/04100

§ 371 Date: Jan. 19, 2000

§ 102(e) Date: Jan. 19, 2000

(87) PCT Pub. No.: WO99/07767

PCT Pub. Date: Feb. 18, 1999

(30) Foreign Application Priority Data

Aug. 7, 1997 (DE) .......................................... 197 34 245

(51) Int. Cl.$^7$ .............................................. C08G 77/08
(52) U.S. Cl. .............................. 528/23; 528/15; 528/31; 528/26
(58) Field of Search .............................. 528/31, 23, 15, 528/26

(56) References Cited

U.S. PATENT DOCUMENTS

| 4,381,396 | A | | 4/1983 | Ryang |
|---|---|---|---|---|
| 4,404,350 | A | | 9/1983 | Ryang |
| 4,598,135 | A | | 7/1986 | Buese |
| 4,605,567 | A | | 8/1986 | Muller et al. |
| 5,627,253 | A | * | 5/1997 | Nakashima et al. .......... 528/31 |

FOREIGN PATENT DOCUMENTS

| EP | 0 328 027 A2 | 8/1989 |
|---|---|---|
| EP | 0 719 818 A1 | 7/1996 |
| GB | 2 131 038 A | 6/1984 |
| GB | 2 143 246 A | 2/1985 |

* cited by examiner

*Primary Examiner*—Margaret G. Moore
(74) *Attorney, Agent, or Firm*—Brooks & Kushman P.C.

(57) ABSTRACT

The invention relates to a method for producing Si—H containing siliconimides by achieving balanced proportions of organosilicon compounds containing Si—H groups, in siliconimides. It also relates to siliconimides containing Si—H groups and their applications as Si—H comb-crosslinking agents, as a constitutional unit for spread coating paper or electrical components, in adhesive material, moulding material, film material, coating material, laminated material, tough elastomers and composite matrix material.

13 Claims, No Drawings

SILICONIMIDES CONTAINING SI-H GROUPS

TECHNICAL FIELD

Silicone imides containing Si—H groups

DESCRIPTION OF THE RELATED ART

The invention relates to a process for the preparation of silicone imides containing Si—H groups, silicone imides containing Si—H groups and their uses.

Silicone imides containing Si—H groups are known, for example, from GB-A-2143246. However, these silicone imides have the disadvantage that they contain ethylene groups in the main chain and therefore are not as stable as compounds which have only Si—O units in the main chain. Furthermore, these compounds are prepared such that where they have Si—H groups in the main chain, the formation of branchings which render the total compound insoluble is probable.

Silicone imides which under certain circumstances contain Si—H groups are moreover known, for example, from EP-A-328027. However, these compounds are heated to 160–170° C. during the imidation during the preparation, water being liberated, so that the hydrolysis-sensitive Si—H groups are converted in an uncontrolled manner, at least partly, into Si—OH or Si—O groups.

SUMMARY OF THE INVENTION

U.S. Pat. No. 4,598,135 A describes a process for equilibrating organosiloxanes containing Si—H groups into norbonanedicarboxylic acid anhydride-organo-siloxanes.

There is therefore the object of providing silicone imides containing Si—H groups which contain neither alkylene groups in the main chain nor an uncontrollable number of Si—OH groups.

The invention relates to a process for the preparation of silicone imides containing Si—H groups by equilibrating organosilicon compounds containing Si—H groups into silicone imides.

DESCRIPTION OF THE PREFERRED EMBODIMENTS

Preferably, polymeric silicone imides which contain Si—H groups and are composed of optionally siloxane units of the general formula (I)

$$R_aSiO_{(4-a)/2} \quad (I),$$

at least one siloxane unit of the general formula (II)

$$H_bR_cSiO_{(4-b-c)/2} \quad (II)$$

and at least one silicone imide unit of the general formula (III)

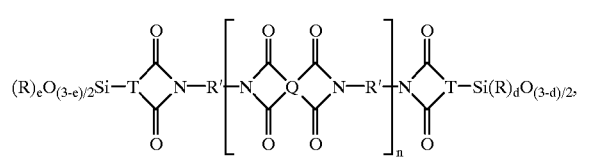

are prepared by a procedure in which organosilicon compounds which are built up from at least one siloxane unit of the general formula (II) and optionally siloxane units of the general formula (I) are equilibrated into silicone imides which are composed of at least one silicone imide unit of the general formula (III) and optionally siloxane units of the general formula (I), wherein R denotes a monovalent radical, namely hydrogen or an unsubstituted or substituted $C_1$–$C_{20}$-hydrocarbon radical, T denotes a trivalent substituted or unsubstituted aliphatic $C_1$–$C_{18}$-hydrocarbon radical or a trivalent substituted or unsubstituted aromatic $C_6$–$C_{18}$-hydrocarbon radical, R' denotes a divalent optionally halogen-substituted aromatic $C_6$–$C_{30}$-hydrocarbon radical, $C_2$–$C_{20}$-alkylene or cycloalkylene radical or a divalent radical of the general formula (IV)

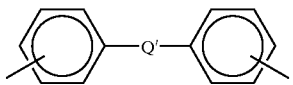

Q' denotes a chemical bond or a divalent optionally halogen-substituted organic $C_1$–$C_{20}$-radical, Q denotes a tetravalent aromatic radical which is chosen from the groups

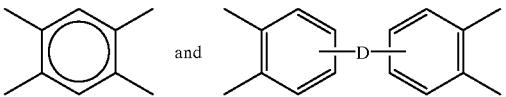

wherein

D is chosen from the groups:
—S(O)—$_2$—, —$C_xH_{2x}$—, —C(O)—O—R'—O—C(O) and —O—R'—O—,
x denotes an integer from 1 to 5,
a denotes the values 0, 1, 2 or 3,
b denotes the values 1, 2 or 3,
c denotes the values 0, 1 or 2,
d denotes the values 0, 1, 2 or 3,
e denotes the values 0, 1, 2 or 3 and
n denotes an integer from 0 to 300.

If d and/or e have the value 3, the particular silicone groups are in the terminal position.

The hydrocarbon radicals R can be alkyl, cycloalkyl, alkenyl, aryl, aralkyl or alkylaryl groups. R preferably denotes alkyl radicals having 1 to 10 carbon atoms, such as methyl, ethyl, propyl, isopropyl, butyl, isobutyl, n-pentyl, isopentyl, neopentyl and tert-pentyl; cycloalkyl radicals having 5 to 8 carbon atoms, such as cyclopentyl, cyclohexyl, methylcyclohexyl, ethylcyclohexyl, cycloheptyl and norbornyl radicals; alkenyl radicals having 2 to 15 carbon atoms, such as vinyl, allyl, n-5-hexenyl, 4-vinylcyclohexyl and 3-norbornenyl; aryl radicals having 6 to 30 carbon atoms, such as phenyl, biphenyl, anthryl, phenanthryl and naphthyl; aralkyl radicals, such as benzyl, 1- or 2-phenylethyl, 1-, 2- or 3-phenylpropyl, o-methylphenylethyl, 3,5-dimethylphenylethyl, p-bromophenylethyl, o-bromophenylethyl, 3,5-dibromophenylethyl, p-chlorophenylethyl and 3,5-dichlorophenylethyl; and alkylaryl radicals, such as o-, m- and p-tolyl and xylyl. Examples of substituted hydrocarbon radicals as the radical R are halogenated hydrocarbon radicals, such as the chloromethyl, 3-chloropropyl, 3-bromopropyl, 3,3,3-trifluoropropyl, trifluorotolyl and 5,5,5,4,4,3,3-heptafluoropentyl radical, and the chlorophenyl, dichlorophenyl and trichlorotolyl radical; mercaptoalkyl radicals, such as the 2-mercaptoethyl and 3-mercaptopropyl radical; cyanoalkyl radicals, such as the 2-cyanoethyl and 3-cyanopropyl radical; acyloxyalkyl radicals, such as the 3-acryloxypropyl and 3-methacryloxypropyl radicals; acetoxyalkyl radicals, such as the 3-acetoxypropyl radical; succinic acid anhydride-alkyl radicals, such as the 3-succinic acid anhydride-propyl radical; phthalimidoalkyl radicals; ether radicals, such as the methoxyethylene glycol oxypropyl radical and methoxypolyethylene glycol ether propyl radical and epoxy radicals, such as the glycidyloxypropyl radical, methyl, ethyl, propyl and phenyl being preferred.

The trivalent hydrocarbon radicals T are, for example,

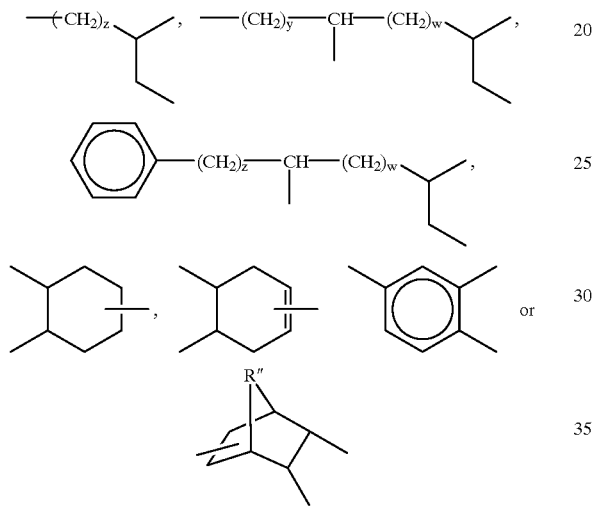

wherein z denotes the values 0, 1, 2 or 3, w denotes the values 1 or 2, y denotes the values 0 or integers from 1 to 16 and R" denotes —O—, —CH$_2$—, —(CH$_2$)$_2$— or —CH=CH—.

The divalent hydrocarbon radical R' preferably denotes the following groups

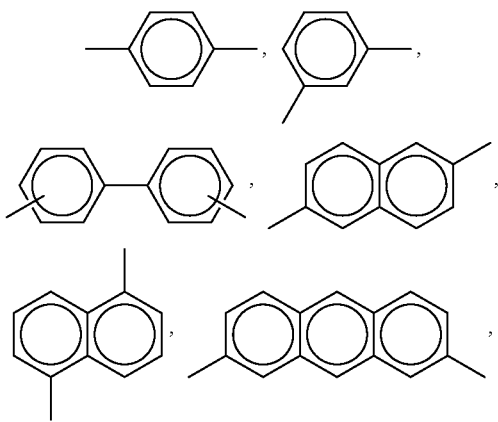

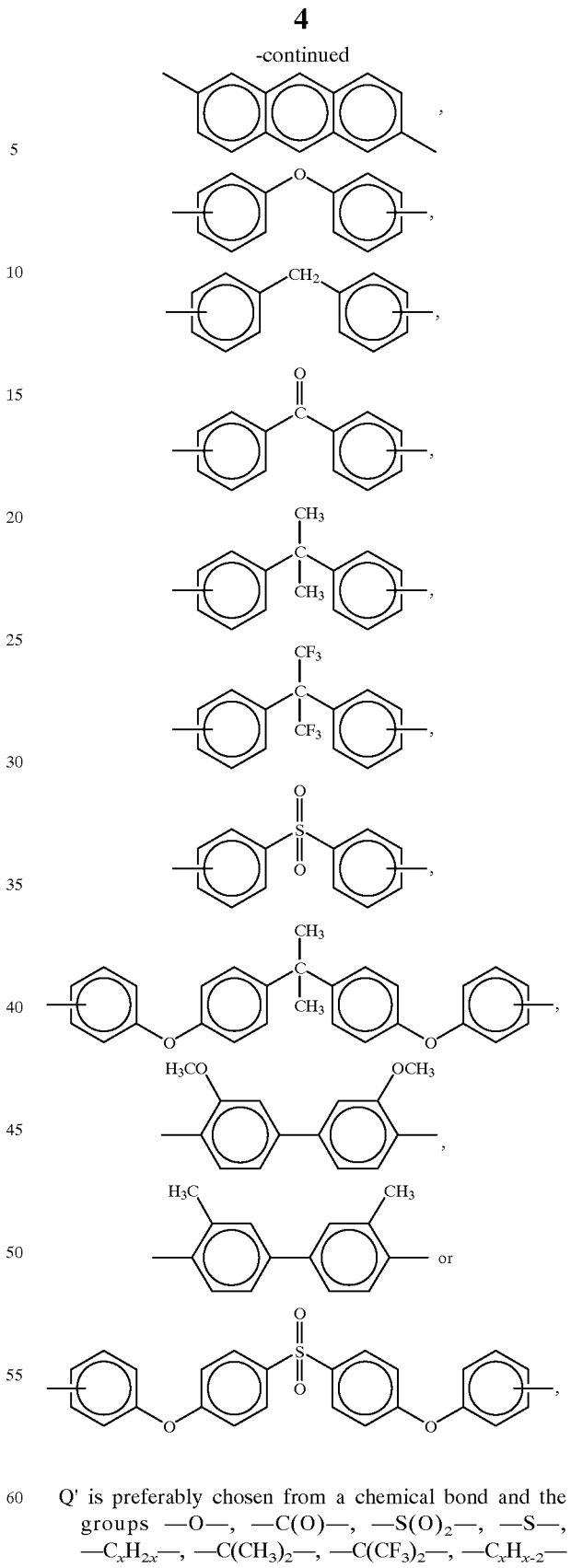

Q' is preferably chosen from a chemical bond and the groups —O—, —C(O)—, —S(O)$_2$—, —S—, —C$_x$H$_{2x}$—, —C(CH$_3$)$_2$—, —C(CF$_3$)$_2$—, —C$_x$H$_{x-2}$— or —O—C$_6$H$_4$—Q"—C$_6$H$_4$—O—.

Q" is preferably chosen from a chemical bond and the groups —O—, —C(O)—, —S(O)$_2$—, —S—, —C$_x$H$_{2x}$—, —C(CH$_3$)$_2$—, —C(CF$_3$)$_2$— or C$_x$H$_{x-2}$.

The following units can be employed, for example, for Q:

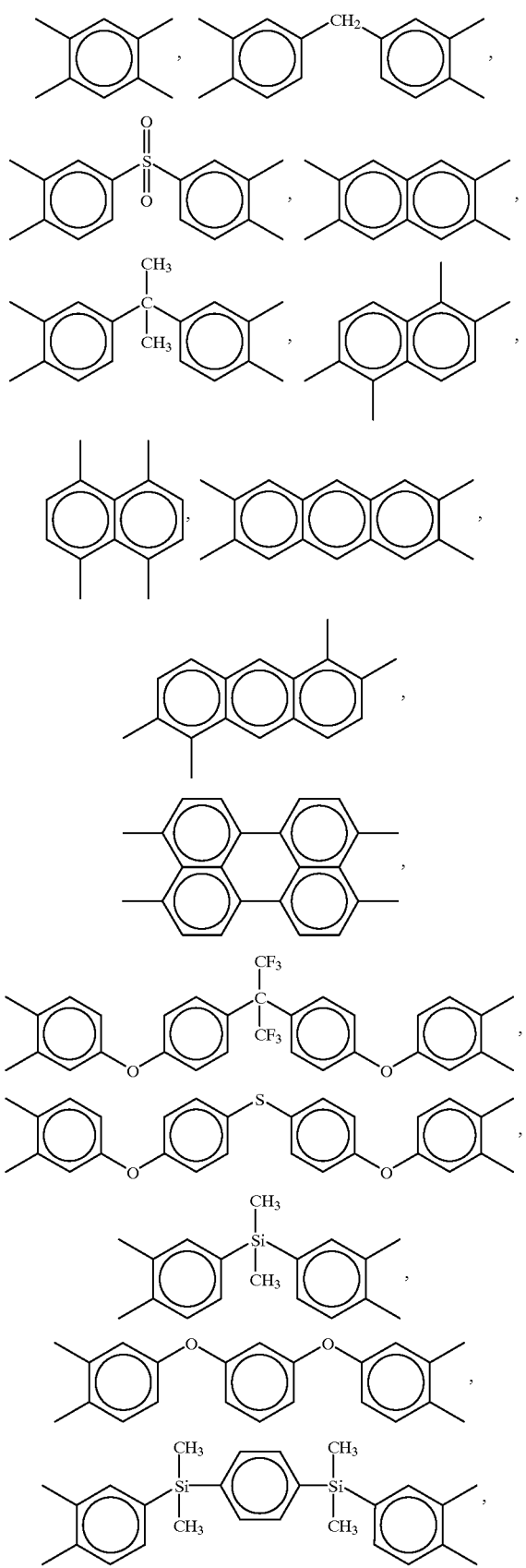

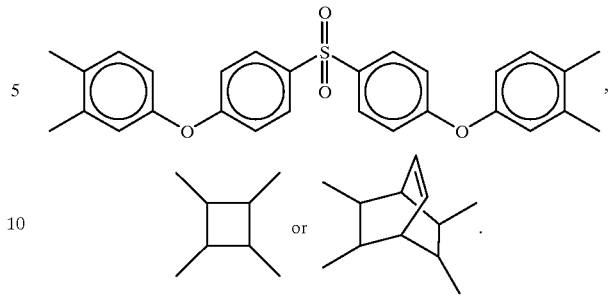

The polymeric silicone imides containing Si—H groups can contain predominantly silicone contents, comparable contents of silicone content and imide content or predominantly imide contents.

Preferably, the polymeric silicone imides containing Si—H groups contain 0.001–99.6 mol %, articularly preferably 0.1–25 mol %, in particular 5–20 mol % of the general formula (I), 0.14–99.8 mol %, particularly preferably 60–99.5 mol %, in particular 75–95 mol % of the formula (II) and 0.2–99.5 mol %, particularly preferably 0.5 to 40 mol %, in particular 1–15 mol % of the general formula (III).

The preparation of the starting silicone imides which are composed of units of the general formula (III) and optionally siloxane units of the general formula (I) is described, for example, in U.S. Pat. No. 4,404,350.

The organosilicon compounds containing Si—H groups which are built up from at least one siloxane unit of the general formula (II) and optionally siloxane units of the general formula (I) can be cyclic and/or open-chain polymers. Preferably, the organosilicon compounds containing Si—H groups have at least three Si—H groups per molecule. Examples of the organosilicon compounds containing Si—H groups which can be employed in the process according to the invention are cyclic organohydridosiloxanes, such as siloxanes of the general formula $(HSiR_3)_u$, in which u denotes the values 3 to 10, in particular 3 to 6, and R has the above meanings, preferably methyl, ethyl, propyl and phenyl radicals. Tetramethylcyclotetrasiloxane, pentamethylcyclopentasiloxane and hexamethylcyclohexasiloxane are particularly preferred.

Further examples of the organosilicon compounds containing Si—H groups which can be employed in the process according to the invention are linear organohydridosiloxanes, such as organohydridosiloxanes which are preferably blocked on both ends by triorganosilyl or diorganosilyl groups, diorganosiloxane/organohydridopolysiloxane copolymers, or mixtures of two or more of these compounds. Linear organohydridosiloxanes of the general formula $R_3Si—(—O—SiH(R))_v—O—SiR_3$, in which v denotes the values 3 to 100, in particular 3 to 50, and R has the above meanings, preferably methyl, ethyl, propyl and phenyl radicals, are particularly preferred.

The process is preferably carried out in the presence of a catalyst. Catalysts which can be employed in the process according to the invention are any desired acid catalysts with which an equilibration of organo(poly)siloxanes is usually promoted. Examples of such catalysts are toluenesulphonic acid, sulphuric acid, phosphoric acid, trifluoromethanesulphonic acid, trifluoroacetic acid, aluminium sulphate dihydrate, phosphonitrilic chlorides, acid catalysts which are solid under the reaction conditions, such as acid-activated bleaching earth, acid zeolites and sulphonated charcoal, and sulphonated styrene/divinylbenzene copolymer. Preferred catalysts are toluenesulphonic acid, sulphuric acid, trifluoroacetic acid, trifluoromethanesulphonic acid, phosphonitrilic chlorides and acid-activated bleaching earth. Sulphuric acid, phosphonitrilic chlorides and acid-activated bleaching earth are particularly preferred. The catalysts are added in amounts of 0.001 to 10% by weight, preferably in amounts of 0.001 to 5% by weight, and particularly preferably 0.002 to 3% by weight, in each case based on the weight of silicone imide and organosilicon compound containing Si—H groups. The reaction can be carried out without or in the presence of solvents. Examples of solvents which are used according to the invention are alkane mixtures having a boiling range from 80 to 110° C. at 1 bar (abs.), benzene, toluene, xylenes, chlorobenzene, dichlorobenzene, halogenated alkanes having 1 to 6 carbon atoms, such as methylene chloride, chloroform, trichloroethylene and perchloroethylene, and ethers, such as tetrahydrofuran, 1,2-dimethoxyethane, diethylene glycol dimethyl ether, triethylene glycol dimethyl ether, di-n-butyl ether and mixtures of at least two such solvents. Toluene, xylenes, methylene chloride and tetrahydrofuran are preferred. Toluene is particularly preferably used. If the reaction is carried out in the presence of solvents, the preferred amount of solvent is 10 to 90% by weight, particularly preferably 40 to 80% by weight, based on the total weight of silicone imide, organosilicon compound containing Si—H groups and solvent.

The process according to the invention can be carried out under the pressures (0.5 to 10 bar) and at the temperatures (from 20° C. to 200° C.) used hitherto in the equilibration of organo(poly)siloxanes. The pressure is particularly preferably the same as the pressure of the surrounding atmosphere, i.e. about 1 bar (abs.), or the hydrostatic pressure of the column of liquid in the reaction vessel. The preferred temperature is 20° C. to 200° C., preferably 20° C. to 150° C., the particularly preferred temperature being 25° C. to 120° C. As a rule, the reaction time is 30 minutes to 72 hours, depending on the starting materials, temperature, catalyst and solvent.

The reaction can be carried out under air or under an inert gas, such as, for example, nitrogen or argon. The reaction is preferably carried out under nitrogen as an inert gas, with exclusion of moisture from the atmosphere.

The invention also relates to polymeric silicone imides which contain Si—H groups and are composed of optionally siloxane units of the general formula (I)

$$R_aSiO_{(4-a)/2} \quad (I),$$

at least one siloxane unit of the general formula (II)

$$H_bR_cSiO_{(4-b-c)/2} \quad (II)$$

and at least two silicone imide units of the general formula (III)

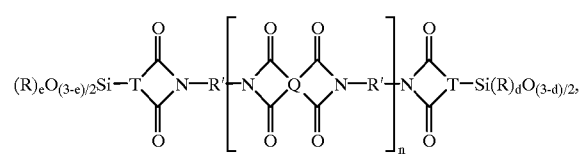
(III)

wherein

R is a monovalent radial, namely hydrogen or a $C_1$–$C_{20}$-hydrocarbon radical which is unsubstituted or substituted by fluorine, chlorine, bromine, mercapto, cyano, acyloxy, acetoxy, succinic acid anhydride, phthalimide, ether and epoxy radicals and T denotes a trivalent hydrocarbon radical which is chosen from

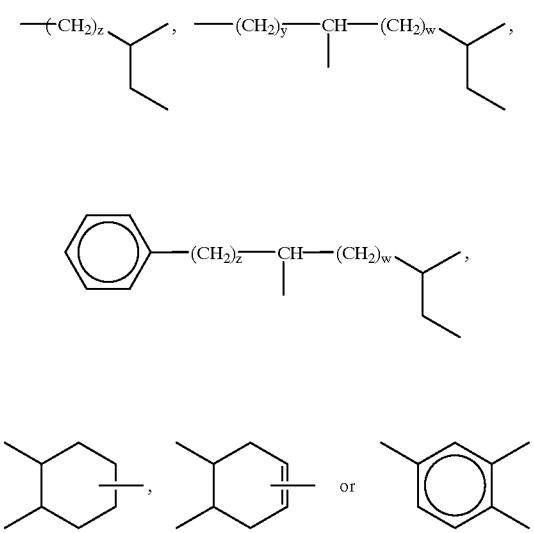

and R', Q, a, b, c, d, e and n have the meanings given in claim 2.

T, R', Q, a, b, c, d, e and n have the above meanings.

The present invention also relates to the use of polymeric silicone imides containing Si—H groups as Si—H comb crosslinking agents and as a unit, for example, for coatings of paper and electrical elements, for example insulation and/or protective jackets on electrical leads and switch elements and circuits, in adhesives, moulding compositions, films, coverings, laminates and tough elastomers, and in matrix materials for composite materials, such as glass fibre, carbon fibre or polyaramid fibre composites, such as kevlar-polyaramid fibre composites.

In the following examples, unless stated otherwise, a) all the amounts stated are based on the weight, and all the parts stated are parts by weight;

b) all the pressures are 0.10 MPa (abs.);

c) all the temperatures are 20° C.

EXAMPLES

Example 1

200 g of an α,ω-silicone-bis-propylsuccinic acid dianhydride prepared analogously to U.S. Pat. No. 4,605,567, 39 g of 4,4-diaminodiphenylmethane, 8 g of 2-hydroxypyridine and 600 ml of 1,2-dichlorobenzene were mixed and the mixture was heated under reflux. When the solution had cooled, 100 ml of methylene chloride were added to the mixture and the resulting homogeneous product mixture was poured into methanol. Reprecipitation from methylene chloride/methanol was repeated. A product precipitated out and was dried. From the preparation method and IR and NMR spectroscopy, the product was a silicone imide which essentially comprised the following units A) imide unit

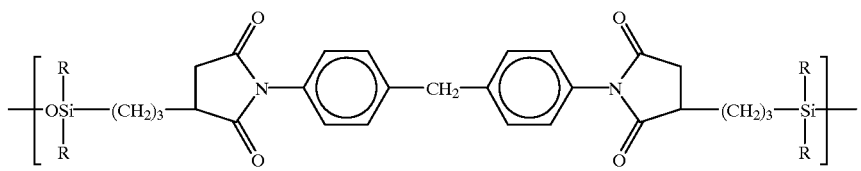

and B) siloxane unit

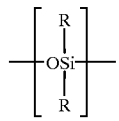

wherein R in principle represents methyl and the polymer was composed of 10 mol % of imide units and 90 mol % of siloxane units.

30.0 g of the silicone imide, 60.0 g of siloxane hydride of the formula $Me_3Si-(-O-SiH(Me))_n-O-SiMe_3$ (n is about 35, commercially obtainable from Aldrich GmbH and Co. KG), 150 g of toluene (dried) and 0.09 g of concentrated sulphuric acid were stirred under an inert gas for 3 hours at 100° C. The mixture was filtered, the solvent was removed and the product was dried in vacuo. 72 g of a highly viscous oil were obtained. On the basis of the preparation method, and IR and NMR spectra, the product was a silicone imide containing Si—H groups and with predominantly trimethylsilyl groups on the polymer ends, which chiefly had the following composition:

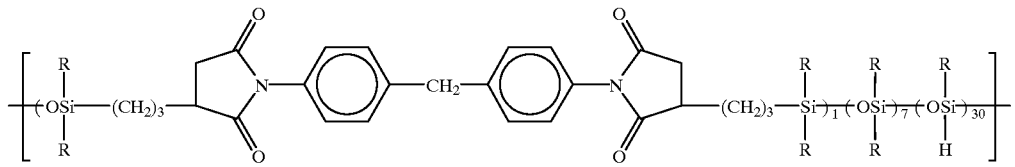

The characteristic absorption bands in the IR spectrum (NaCl plates) were at 2167 cm$^{-1}$ vs (Si—H); 1714 cm$^{-1}$ m (imide) ; 1261 cm$^{-1}$ vs (Si—CH$_3$) and 1097 cm$^{-1}$ vs (Si—O—Si). $^{29}$Si—NMR: (CDCl$_3$), δ=10–7 ppm (Si—O—), 18–21 ppm for —O—Si(Me)$_2$—O— and 33–35 ppm (—O—SiH(Me)—O—). The ratio of the integrals corresponded to the indices in the above formula.

Example 2

30.0 g of the silicone imide from Example 1, 60.0 g. of siloxane hydride of the formula $Me_3Si-(-O-SiH(ME))_n-O-SiMe_3$ (n is about 35, commercially obtainable from Aldrich GmbH & Co KG), 150 g of toluene (dried) and 0.20 g of trifluoromethanesulphonic acid were stirred at about 65° C. After 48 hours, the resulting homogeneous solution was cooled to room temperature. The solution was filtered and freed from the solvent and the product was dried in vacuo. 67 g of a highly viscous oil were obtained. On the basis of the preparation method, IR spectrum and NMR spectra, the product was a silicone imide containing Si—H groups with predominantly trimethylsilyl groups at the polymer ends, which was similar in composition to the product from Example 1.

Example 3

30.0 g of the silicone imide from Example 1, 125.0 g of siloxane hydride of the formula $Me_3Si-(-O-SiH(Me))_n-O-SiMe_3$ (where n is about 35, commercially obtainable from Aldrich GmbH & Co KG), 250 g of toluene (dried) and 0.20 g of concentrated sulphuric acid were stirred under an inert gas at 100° C. for 3 hours. The mixture was filtered, the solvent was removed and the product was dried in vacuo. 110 g of a clear oil were obtained. On the basis of the preparation method and IR and $^1$H— and $^{29}$Si—NMR spectra, the product was a silicone imide containing Si—H groups with predominantly trimethylsilyl groups at the polymer ends, which chiefly had the following composition, wherein R is in principle methyl:

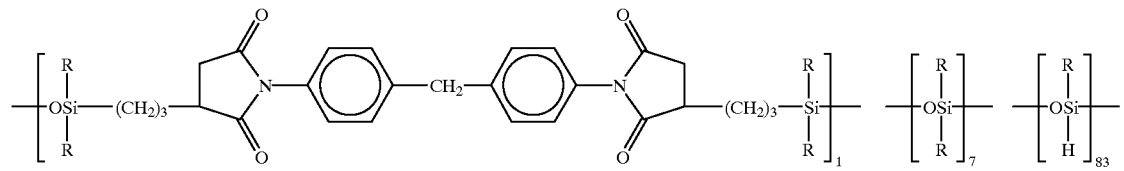

Use Example 1 (release paper coating)

The Si—H comb crosslinking agent from Example 3 (amount of crosslinking agent was chosen such that the Si—H/vinyl ratio in Use Example 1 and Comparison Example 1 was the same) was mixed with a polymer containing vinyl groups, Pt catalyst and inhibitor and the mixture was applied in a thin layer (4 g/m²) to glassine paper, Buxil® N 925, 65 g/cm² (from Bosso), using a glass rod. The coating was crosslinked at 150° C. It was then glued with rubber adhesive T-4154 or acrylate adhesive A-7475 (both from Beiersdorf). After ageing for 20 hours at 70° C. under a load of 70 g/cm², the peel force was determined by the Finat test method 4, 10 and 11.

Comparison Example 1

An H-siloxane comprising —O—SiH(Me) groups and with trimethylsilyl groups at the polymer ends was employed in the above recipe instead of the crosslinking agent.

The peel force in [cN/cm] required to peel off the paper was determined as follows:

A) with respect to acrylate adhesive A-7475:

| Rate of peeling | 0.3 m/min | 10 m/min | 50 m/min | 100 m/min | 200 m/min | 300 m/min |
|---|---|---|---|---|---|---|
| Example 1 | 24 | 45 | 83 | 99 | 107 | 106 |
| Comparison Example 1 | 7 | 12 | 32.0 | 41 | 42 | 45 |

B) with respect to rubber adhesive T-4154:

| Rate of peeling | 0.3 m/min | 10 m/min | 50 m/min | 100 m/min | 200 m/min | 300 m/min |
|---|---|---|---|---|---|---|
| Example 1 | 16 | 25 | 36 | 41 | 57 | 49 |
| Comparison Example 1 | 8 | 10 | 14.6 | 20 | 28 | 29 |

What is claimed is:

1. A process for the preparation of silicone imides containing Si—H groups, said process comprising equilibrating organosilicon compounds containing Si—H groups into silicone imides.

2. The process of claim 1, wherein polymeric silicone imides which contain Si—H groups and are composed of a) optionally, siloxane units of the general formula (I)

b) at least one siloxane unit of the general formula (II)

c) at least one silicone imide unit of the general formula (III)

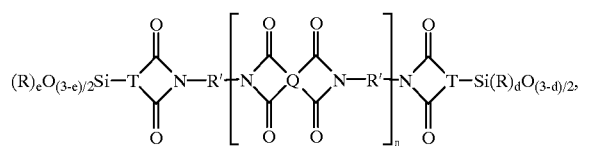

are prepared by equilibrating organosilicon compounds containing at least one siloxane unit of the general formula (II) and optionally siloxane units of the general formula (I) into silicone imides comprising at least one silicone imide unit of the general formula (III) and optionally siloxane units of the general formula (I), wherein R is silicon-bonded hydrogen or a silicon-bonded monovalent organic radical, T is a trivalent substituted or unsubstituted aliphatic $C_1$–$C_{18}$-hydrocarbon radical or a trivalent substituted or unsubstituted aromatic $C_6$–$C_{18}$-hydrocarbon radical, R' is a divalent optionally halogen-substituted aromatic $C_6$–$C_{30}$-hydrocarbon radical, $C_2$–$C_{20}$-alkylene or cycloalkylene radical, or is a divalent radical of the general formula (IV)

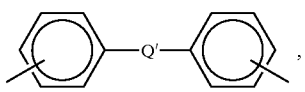

Q' is a chemical bond or a divalent optionally halogen-substituted organic $C_1$–$C_{20}$-radical, Q is a tetravalent aromatic radical independently selected from the group consisting of

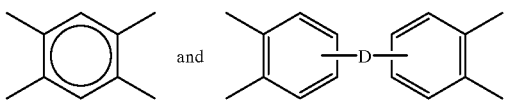

wherein

D is selected from the group consisting of
—S(O)$_2$—, —C$_x$H$_{2x}$—, —C(O)—O—R'—O—C(O)— and —O—R'—O—, x is an integer from 1 to 5, a is 0, 1,2 or 3, b is 1, 2 or 3, c is 0, 1 or 2, d is 0, 1, 2 or 3, e is 0, 1, 2 or 3 and n is an integer from 0 to 300.

3. The process of claim 2, wherein each R independently is silicon-bonded hydrogen or an optionally substituted, silicon-bonded $C_1$–$C_{20}$ hydrocarbon radical.

4. The process of claim 1, wherein said step of equilibrating takes place in the presence of an acid equilibration catalyst.

5. The process of claim 2, wherein said step of equilibrating takes place in the presence of an acid equilibration catalyst.

6. The process of claim 3 wherein said step of equilibrating takes place in the presence of an acid equilibration catalyst.

7. In a polymer-containing Si—H comb crosslinking agent, paper coating, coating for an electrical element, adhesive, molding composition, film, covering, laminate, or composite material matrix, the improvement comprising selecting as at least a portion of said polymer, a polymeric silicone imide prepared by the process of claim 1.

8. A release-coated substrate, wherein the release coating of said release-coated substrate comprises the hydrosilylation reaction product of a polymer containing hydrosilylatable unsaturated groups, and the Si—H functional silicone imide prepared by the process of claim 1, in the presence of an effective amount of a hydrosilylation catalyst.

9. A polymeric silicone imide containing Si—H groups, comprising a) optionally, siloxane units of the general formula (I)

 (I), b) at least one siloxane unit of the general formula (II)

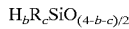 (II), and c) at least two silicone imide units of the general formula (III)

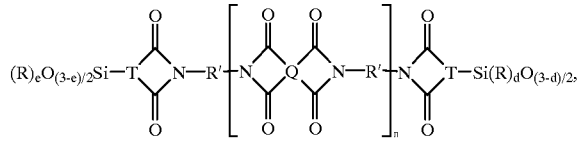 (III)

wherein
R is silicon-bonded hydrogen or a silicon-bonded monovalent organic radical,
R' is a divalent optionally halogen-substituted aromatic $C_6$–$C_{30}$-hydrocarbon radical, $C_2$–$C_{20}$-alkylene or cycloalkylene radical, or is a divalent radical of the general formula (IV)

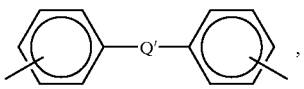 (IV)

Q' is a chemical bond or a divalent optionally halogen-substituted organic $C_1$–$C_{20}$-radical,
Q is a tetravalent aromatic radical independently selected from the group consisting of

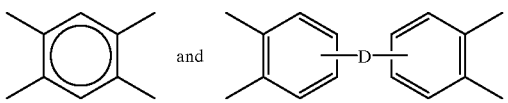

wherein
D is selected from the group consisting of
—S(O)$_2$—, —C$_x$H$_{2x}$—, —C(O)—O—R'—O— C(O)— and —O—R'—O—,
x is an integer from 1 to 5,
a is 0, 1, 2 or 3,
b is 1, 2 or 3,
c is 0, 1 or 2,
d is 0, 1, 2 or 3,
e is 0, 1, 2 or 3,
n is an integer from 0 to 300,
T is a trivalent hydrocarbon radical independently selected from the group consisting of

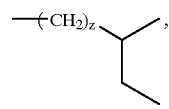

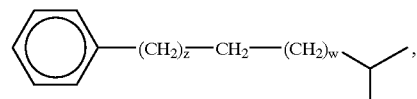

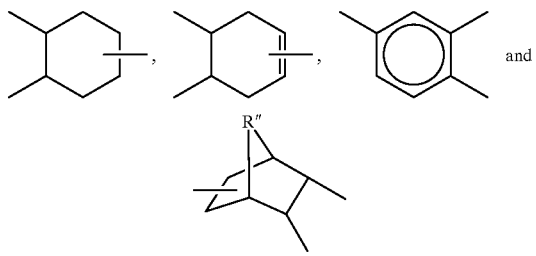

wherein
z denotes the values 0, 1, 2 or 3,
w denotes the values 1 or 2, and
R" denotes —O—, —CH$_2$—, —(CH$_2$)$_2$— or —CH=CH—.

10. The polymeric silicone imide of claim 9, wherein each R independently is silicon-bonded hydrogen or a $C_1$–$C_{20}$ hydrocarbon radical optionally substituted by one or more of fluorine, chlorine, bromine, mercapto, cyano, acyloxy, acetoxy, succinic acid anhydride, phthalimide, ether, or epoxy radicals.

11. In a polymer-containing Si—H comb crosslinking agent, paper coating, coating for an electrical element, adhesive, molding composition, film, covering, laminate, or composite material matrix, the improvement comprising selecting as at least a portion of said polymer, a polymeric silicone imide of claim 9.

12. A release-coated substrate, wherein the release coating of said release-coated substrate comprises the hydrosilylation reaction product of a polymer containing hydrosilylatable unsaturated groups, and the Si—H functional silicone imide of claim 9, in the presence of an effective amount of a hydrosilylation catalyst.

13. The polymeric silicone imide of claim 9, wherein said trivalent hydrocarbon radical T has an additional valence and corresponds to the formula

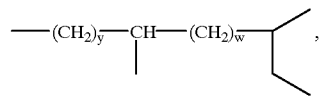

wherein w is as defined in claim 12, and y denotes the value 0 or integers from 1 to 16 and
wherein said additional valence is bonded to an (R)$_e$O$_{(3-e)/2}$Si moiety.

* * * * *